United States Patent [19]
Choi

[11] Patent Number: 5,769,634
[45] Date of Patent: Jun. 23, 1998

[54] DENTAL ARTICULATOR

[76] Inventor: John Choi, 1140L S. Cypress St., La Habra, Calif. 90631

[21] Appl. No.: 867,616

[22] Filed: Jun. 2, 1997

[51] Int. Cl.[6] .................................................. A61C 11/00
[52] U.S. Cl. .............................................. 433/64; 433/34
[58] Field of Search ............................ 433/640 R, 34 R, 433/60, 61, 62, 66

[56] References Cited

U.S. PATENT DOCUMENTS

| | | | |
|---|---|---|---|
| 981,430 | 1/1911 | Kennedy | 433/64 |
| 1,736,006 | 11/1929 | Hagman | 433/64 |
| 2,908,974 | 10/1959 | Stifter | 32/14 |
| 2,928,175 | 3/1960 | Knoth | 433/60 |
| 3,469,314 | 9/1969 | Pearlman | 32/14 |
| 3,765,091 | 10/1973 | Northcutt | 32/14 A |
| 3,775,850 | 12/1973 | Northcutt | 32/14 A |
| 3,922,787 | 12/1975 | Fischer et al. | 433/15 |
| 3,930,311 | 1/1976 | Andrews | 32/14 A |
| 3,964,165 | 6/1976 | Stahl | 32/14 A |
| 4,050,156 | 9/1977 | Chasanoff et al. | 32/2 |
| 4,107,844 | 8/1978 | Kurz | 32/14 A |
| 4,120,090 | 10/1978 | Kesling | 433/23 |
| 4,186,488 | 2/1980 | Wallshein | 433/8 |
| 4,207,677 | 6/1980 | Lampert | 433/60 |
| 4,249,897 | 2/1981 | Anderson | 433/8 |
| 4,299,569 | 11/1981 | Frantz | 433/8 |
| 4,302,532 | 11/1981 | Wallshein | 433/8 |
| 4,353,692 | 10/1982 | Karrakussoglu | 433/16 |
| 4,548,581 | 10/1985 | Huffman | 433/64 |
| 4,674,978 | 6/1987 | Acevedo | 433/8 |
| 4,717,341 | 1/1988 | Goldberg et al. | 433/9 |
| 4,786,253 | 11/1988 | Morais | 433/64 |
| 4,850,865 | 7/1989 | Napolitano | 433/8 |
| 4,894,012 | 1/1990 | Goldberg et al. | 433/215 |
| 5,074,783 | 12/1991 | Reher | 433/8 |
| 5,078,596 | 1/1992 | Carberry et al. | 433/8 |
| 5,141,436 | 8/1992 | Orlowski et al. | 433/226 |
| 5,254,002 | 10/1993 | Reher et al. | 433/8 |
| 5,269,680 | 12/1993 | Kawaguchi | 433/9 |
| 5,302,121 | 4/1994 | Gagin | 433/10 |
| 5,318,440 | 6/1994 | Adam et al. | 433/8 |
| 5,322,436 | 6/1994 | Horng et al. | 433/23 |
| 5,322,613 | 6/1994 | Ohira | 433/2 X |
| 5,358,402 | 10/1994 | Reed et al. | 433/8 |
| 5,360,337 | 11/1994 | Westdyk | 433/64 |
| 5,380,196 | 1/1995 | Kelly et al. | 433/8 |
| 5,425,636 | 6/1995 | Ghim | 433/64 |
| 5,551,319 | 9/1996 | Spaulding et al. | 81/9.22 |
| 5,556,276 | 9/1996 | Roman et al. | 433/23 X |
| 5,678,992 | 10/1997 | Carlson | 433/34 |

FOREIGN PATENT DOCUMENTS

| | | | |
|---|---|---|---|
| 0 316 086 | 5/1989 | European Pat. Off. | A61K 6/08 |
| 0 476 789 | 3/1992 | European Pat. Off. | A61K 6/083 |
| 41 35 434 | 4/1993 | Germany | A61C 7/12 |
| 43 43 275 | 6/1994 | Germany | A61C 7/12 |

OTHER PUBLICATIONS

*Journal of Clinical Orthodontics*, Mar. 1989; Tella Tech Advertisement.
*Journal of Clinical Orthodontics*, Jan. 1989; Product News Column.
*Journal of Clinical Orthodontics*, Sep. 1986; Mirage bracket advertisement.
*American Journal of Orthodontics*, vol 89, No. 6 (Jun. 1986); American Orthodontics Advertisement.
*American Journal of Orthodontics and Dentofacial Orthopedics*, vol. 95, No. 5 (May 1989); Silkon Bracket Advertisement.
*Journal of Clinical Orthodontics*, Sep. 1990; Ormco Advertisement.

*Primary Examiner*—John J. Wilson
*Attorney, Agent, or Firm*—Allen A. Dicke, Jr.

[57] ABSTRACT

The main member of the Dental Articulator is a unitary structure of first and second bodies attached by legs. Each of the legs has a self-hinge. The body each has a socket which receives a ball. The balls each has a tapered spline which engages in the corresponding mold recess in a dental cast. The balls are clampable in the sockets when the dental casts are in proper relative position. The self-hinges permit repeatable opening and closing of the dental cast.

20 Claims, 4 Drawing Sheets

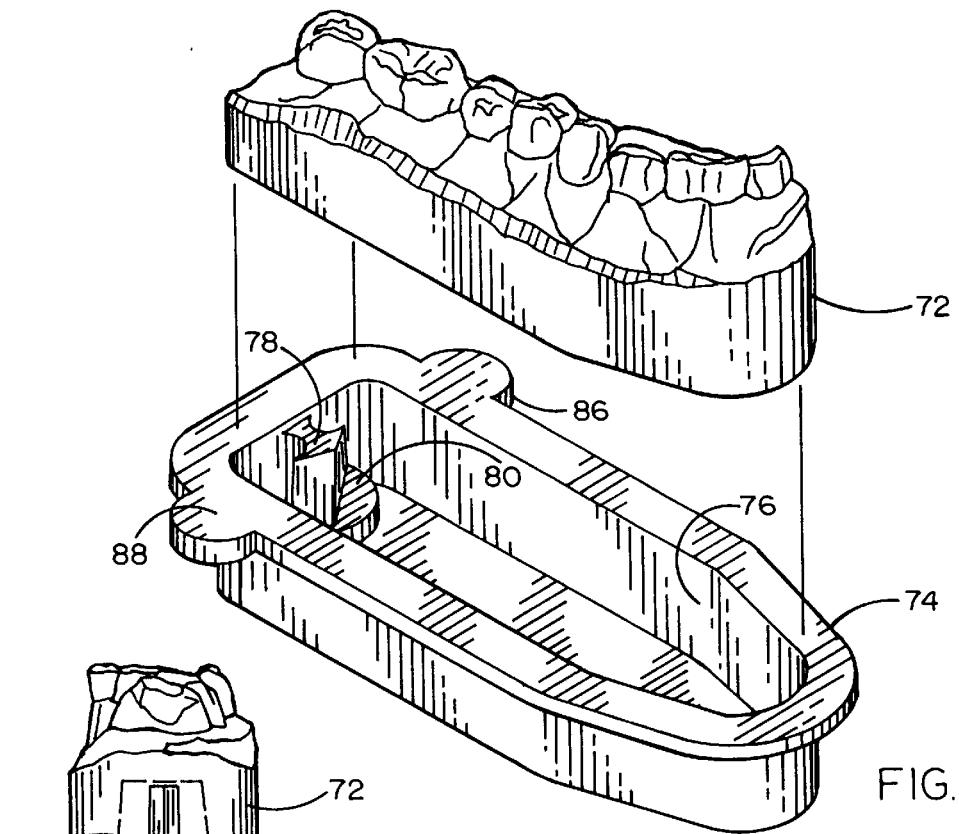
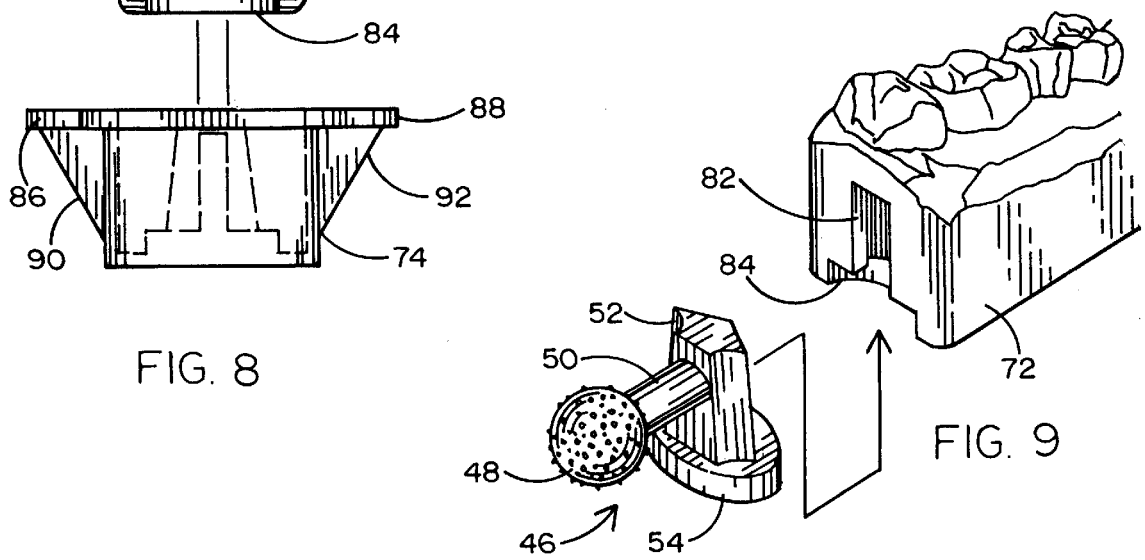
FIG. 7
FIG. 8
FIG. 9

5,769,634

DENTAL ARTICULATOR

FIELD OF THE INVENTION

This invention is directed to an articulator for repeatedly permitting two dental casts to be positioned adjacent each other and moved away from each other, and particularly an inexpensive articulator which can be used several times and then thrown away.

BACKGROUND OF THE INVENTION

Pairs of casts are made of partial or complete dental arches. An articulator is attached to a pair of casts to permit the casts to be moved toward and away from each other. When they are adjacent to each other, the casts represent the closed mouth position and this position must be repeatable. In addition, the casts must be moved away from each other for work on the casts in the preparation of dental prostheses or dental elements. The prostheses may be bridges and the dental elements may be crowns.

In the prior art there have been articulators which were made of metal and which are employed for a large number of reuses. The problem with a metallic articulator is that the dental cast must be adhesively attached thereto. Such attachment takes time for the adhesive to set. Furthermore, after the adhesive has set, if registration is incorrect, the cast must be cut free and reattached. Such is further time consuming.

Attempts have been made to create inexpensive, throwaway, single-use dental articulators. These dental articulators are of single-use because they are adhesively attached to the dental casts. Adhesive attachment takes time during which the technician waits for the dental cast to be sufficiently secured before being used. If the alignment of the two dental casts is incorrect, the glued-on articulator must be cut away and a new attachment must be made. This also consumes the technician's time and expertise. Thus, there is need for an improved dental articulator.

SUMMARY OF THE INVENTION

In order to aid in the understanding of this invention, it can be stated in essentially summary form that it is directed to a dental articulator which has two unitary main members which are hinged with respect to each other on at least three legs. First and second articulator mounts are attached to the two portions of the main member by ball and socket joints which are clampable into fixed positions. The articulator mounts each carry a tapered post which attaches into the two dental casts into a corresponding recess therein. No adhesive is used on the ball and socket joints or on the tapered posts inserted into the dental casts.

It is thus a purpose and advantage of this invention to provide a dental articulator which is capable of positioning two dental casts in appropriate position with respect to each other and permit the casts to be moved apart and returned to the same position, wherein the dental articulator is inexpensive so that it can be utilized for several uses and then thrown away.

It is a further purpose and advantage of this invention to provide dental cast molds which form recesses in the dental casts so that the attachment members on the articulator can be removably inserted therein, yet retain the dental casts in an accurate and repeatable position with respect to the articulator.

It is a further purpose and advantage of this invention to provide a dental articulator which permits adjustment of two dental casts attached thereto, together with locking of the articulator so that the selected position is retained.

It is a further purpose and advantage of this invention to provide a dental articulator which has two stable positions, one of which is where the dental casts are adjacent to each other and another where the dental casts are away from each other so that the dental casts may be worked upon.

Further purposes and advantages of this invention will become apparent from a study of the following specification, the claims and the attached drawings.

BRIEF DESCRIPTION OF THE DRAWINGS

FIG. 7 is an isometric view of a mold for a dental cast, showing a dental cast in projected position with respect thereto.

FIG. 8 is an elevational view of the left end of the mold and cast of FIG. 7.

FIG. 9 is an isometric view of the end of the cast with the attachment means in an exploded position.

DESCRIPTION OF THE PREFERRED EMBODIMENT

Figure 3:
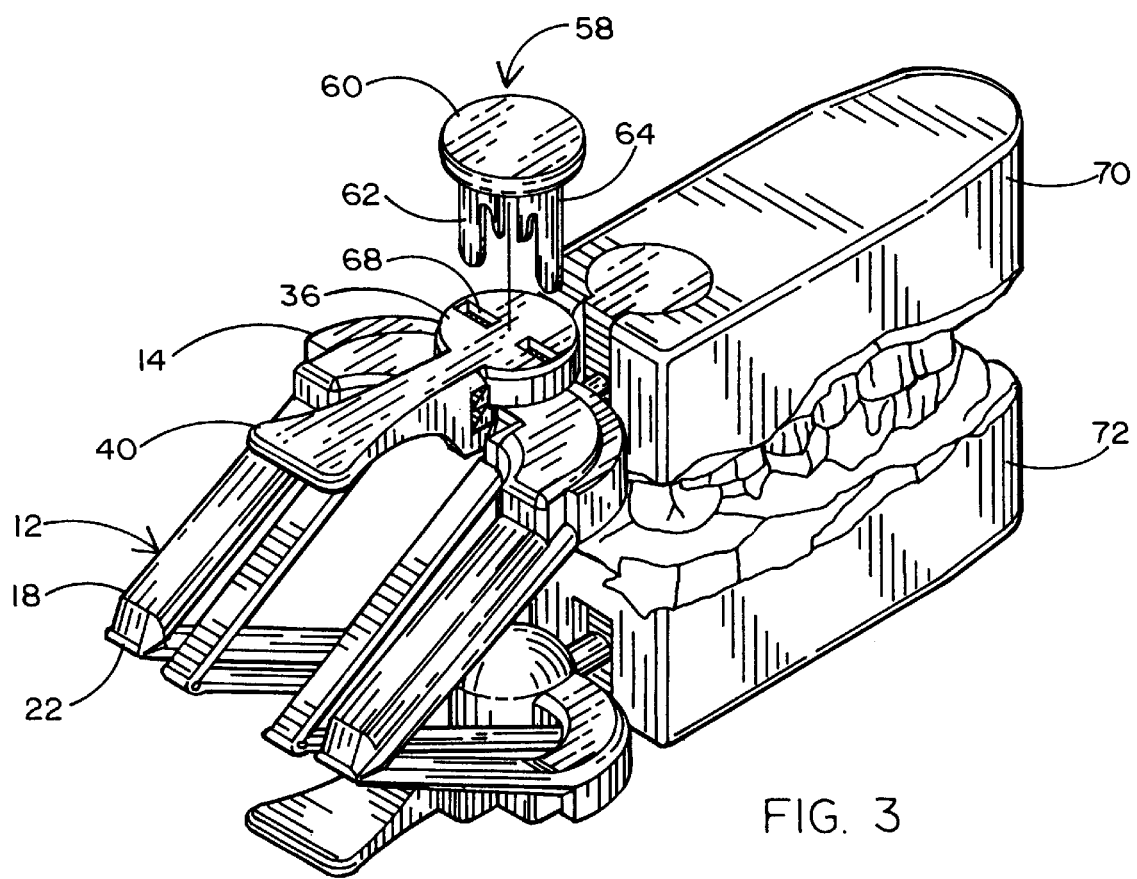
FIG. 3 is an isometric view thereof.
Figure 4:
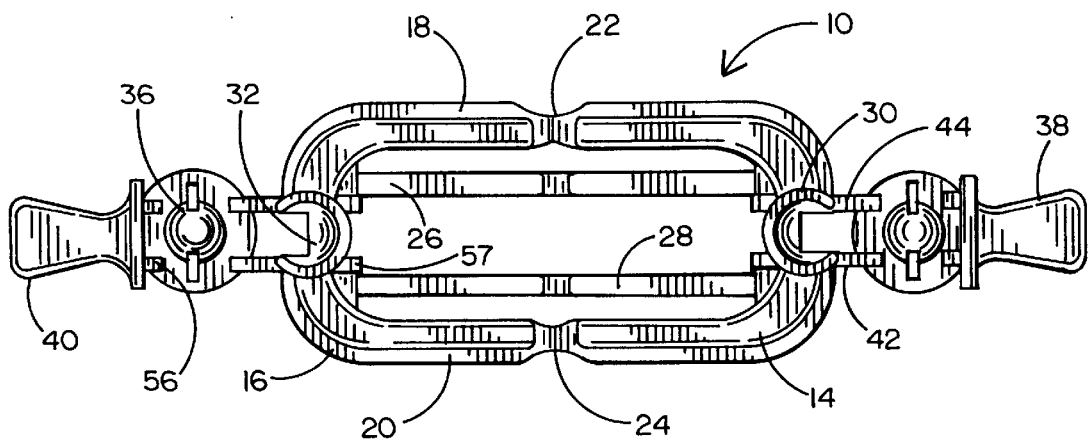
FIG. 4 is a plan view of the main body of the dental articulator in the open position, without showing the attachment means by which the articulator is associated with the dental casts.

The dental articulator of this invention is generally indicated at 10 in FIGS. 1, 2, 3, 4, 5 and 6. The dental articulator 10 has a main member 12 which is unitarily formed by injection molding of a thermoplastic synthetic polymer composition material. The main member has a body at each end. The bodies 14 and 16 are seen in FIGS. 1, 2, 4, 5 and 6. The bodies are joined by a pair of main legs 18 and 20. As seen in FIG. 4, the legs and bodies form an open frame. Self hinges 22 and 24 permit the bodies 14 and 16 to move from the extended position shown in FIGS. 1, 4 and 5 to the closed position shown in FIGS. 2 and 3.

Figure 1:
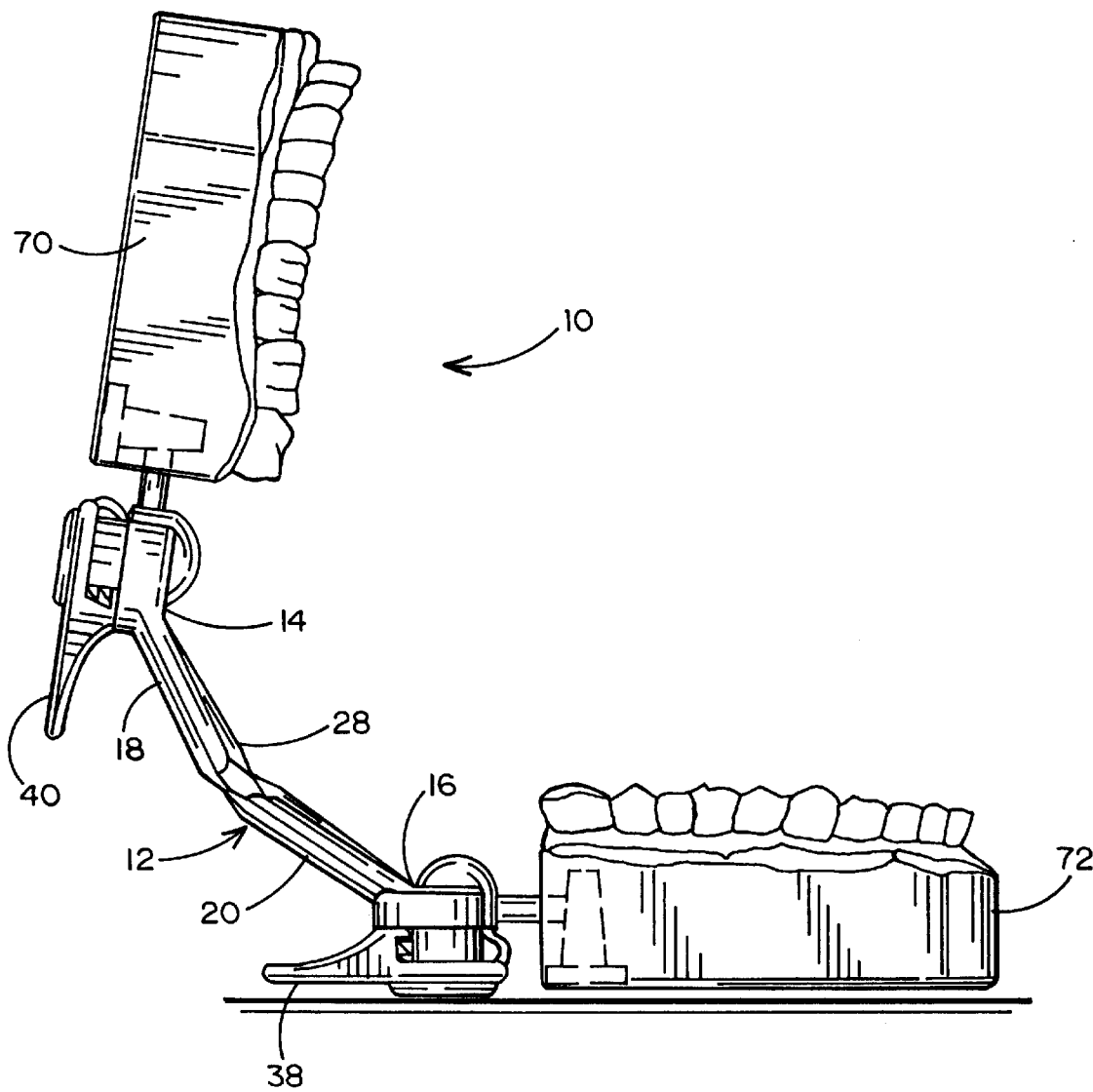
FIG. 1 is a side elevational view of the dental articulator of this invention, shown in association with two dental casts and in the open position.
Figure 2:
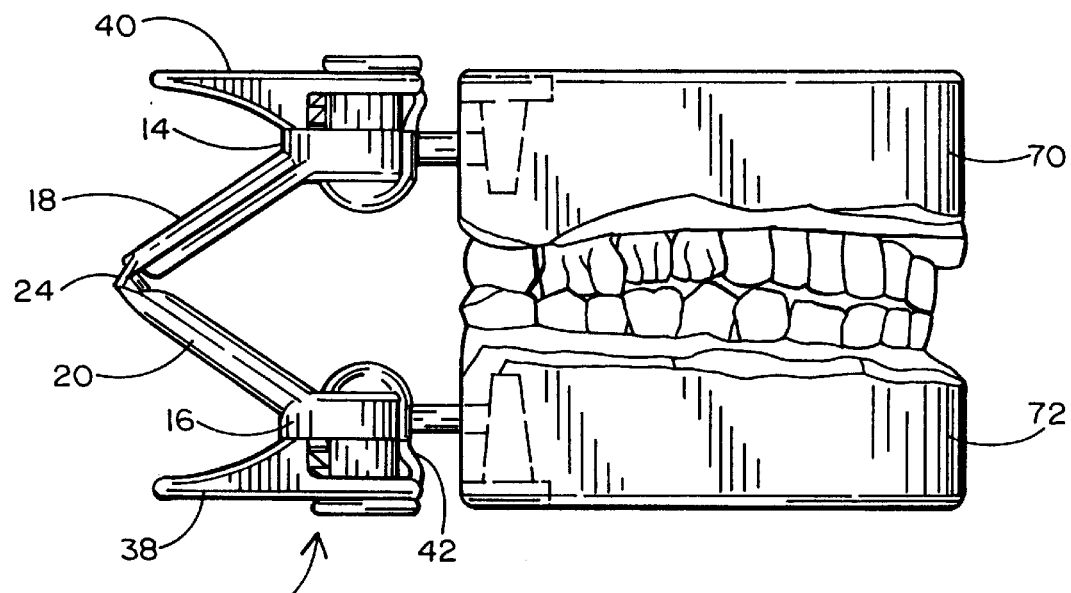
FIG. 2 is a similar view with a dental cast and the articulator in the closed position.

In addition, the bodies 14 and 16 are joined by short legs 26 and 28. These short legs are also integrally formed with the bodies 14 and 16 and have self hinges in line with the hinges 22 and 24. The significance of the short legs 26 and 28 is that they are slightly shorter than the main legs 18 and 20 and thus produce an integral stop position when the bodies are separated as shown in FIG. 1. The shortness of the short legs releasably retains the dental articulator in the open position shown in FIG. 1. Furthermore, the stop provided at this position can be overcome by force to resiliently release the stop condition to permit full opening of the dental articulator to the position shown in FIGS. 4 and 5.

Figure 5:
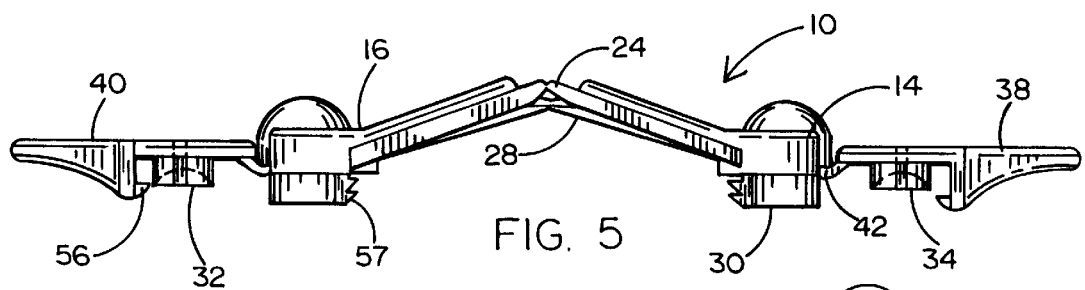
FIG. 5 is an edge view thereof.

Bodies 14 and 16, respectively, carry ball sockets 30 and 32, see FIGS. 4 and 5. Ball socket caps 34 and 36 are integrally formed with the remainder of the main member 12 and are attached by self-hinges to the bodies 14 and 16. The caps are carried on finger levers 38 and 40. The finger levers are hingedly mounted to the adjacent bodies by means of a pair of spaced flexible bands. The spaced flexible bands 42 and 44 are seen in FIG. 4. These flexible bands permit the molding of the ball cap 34 and its finger lever 38 with the molding of the remainder of the main member 12. There are also flexible bands flexibly attaching the finger lever 40 to its body 16. The flexible bands are sufficiently separated so that the ball on the associated attachment means can be inserted therebetween for entry into the ball socket. It is understood that the entire structure shown in FIGS. 4 and 5 is molded together as an integral, one-piece device. The hinges at the center permit movement of the ball sockets around the hinge points and the flexible bands permit the ball sockets to be closed.

Figure 6:
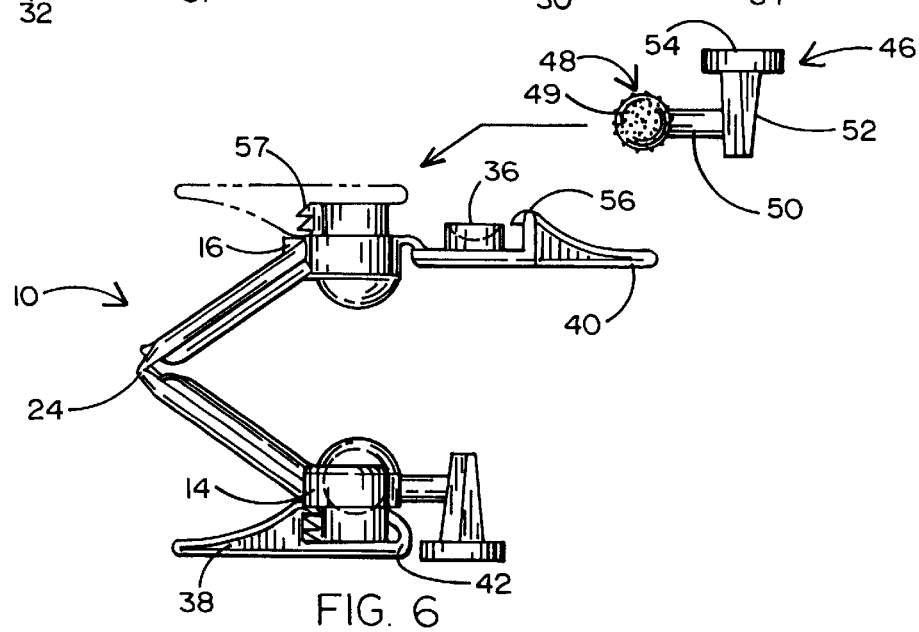
FIG. 6 is an edge view of the main body of the dental articulator, shown in the folded position and shown with the attachment means in association therewith.

One of the attachment members is generally indicated at 46 in FIGS. 6 and 9. Each of the attachment members is identical. Each is comprised of a ball 48 which is mounted on a post 50. The post 50 is mounted on a spline 52. The top of the spline carries thumb pad 54. It is understood that the attachment member 46 is also integrally formed and molded of thermoplastic synthetic polymer composition material. The ball 48 is sized to enter between the flexible bands 42 and 44 and enter the ball socket 30. When in position, the finger levers are brought up and over so that the cap 36 engages on the ball and locks it into the ball socket. A latch 56 engages on a corresponding keeper 57 to releasably hold the cap down over the ball. Each keeper 57, as seen in FIGS. 5 and 6, has two latch teeth. When the finger levers are brought over, each latch engages in the first latch tooth. With this engagement, each ball can still be adjusted. When desired positioning is achieved, the finger levers are pressed so that the latch engages in the second tooth of the keeper, to firmly lock the ball and attachment member. The ball 48 has a roughened and indented surface 49 as seen in FIG. 6, so that once locked in place, the spherical ball is rigid in its cup. Before final locking in the second latch tooth, ball swiveling and adjustment can be made.

In order to aid in repositioning of the dental casts with respect to each other, by repositioning the balls in their sockets, the caps can be released from their latch 56. To provide further assurance of firm locking, locking plunger 58 may optionally be employed. The locking plunger includes a cap 60 to which are secured first and second spears 62 and 64. The locking plunger 58 is seen in FIG. 3. The spears are received into a pair of slots through the cap 36. Slot 68 is shown in FIG. 3. On the other side of the cap is a slot for the other spear 64.

When the technician has aligned the two casts to his satisfaction and has locked the two balls into place, for further security he can insert the locking plunger 58 through the cap 36 and insert a similar locking plunger through the cap 34. When inserted, the spears engage around the ball and slice into the ball on its edges. This makes for a positive locking of the ball into place. Release of the ball for reuse is still permitted by removing the locking plungers, one of which is shown in 58. The dental articulator is thus a device which can position pairs of dental casts in proper relationship to each other and permit moving the dental casts away from each other for work thereon.

The attachment of the articulator to the dental casts is also of significance. Upper and lower dental casts 70 and 72 are shown in FIG. 1. These may be full arch casts or half casts. For drafting convenience, half casts are shown. FIG. 7 shows mold 74 of suitable size and configuration for molding the dental cast 72. In FIG. 7, it is shown in exploded position. The mold has a molding recess 76 of suitable configuration. Within the molding recess and against the mold wall is spear 78 which is mounted on base 80. Base 80 is mounted on the bottom of molding recess 76. When the stone is cast into the recess, the spear and base create spline recess 82 and pad recess 84. The spear 78 joins the wall of the molding recess so that the spline recess is open to the exterior of the cast 72. This spline recess 82 and pad recess 84 are sized to receive spline 52 and pad 54. The thumb pad 54 is provided to forcefully place the spline 52 into its recess.

The spline 52 is preferably substantially in the shape of a truncated pyramid generally of diamond cross section, but it is five-sided so that there is a face onto which the post 50 can be attached. The attachment member 46 is placed with its spline in the spline recess in the dental cast and is forced into place by thumb pressure. The angle toward the apex of this spline is low and thus, the spline is self-locking into place. If it is necessary to remove this spline, it can be done so by inserting a sharp blade at its truncated narrow end. Thus, the attachment members 46 can also be reused. They are not adhesively attached to the dental cast and can be removed when one project is done and reused.

The mold 74 is made of resilient material. The cast 72 is made by placing the casting stone therein when the casting stone is still fluid, at the same time the tooth molding is made on the top of the dental cast. The mold 74 is sufficiently resilient that it can be flexed after the molding stone is hardened. Flexure is aided by the placement of ears 86 and 88 on the edge flanges on the mold. The ears are placed adjacent the spear 78 because the spear presents additional mold surface area against the casting stone. Webs 90 and 92 are triangular in shape, see FIG. 8, to strengthen the ears and when the ears are pressed downward, the walls of the molding recess pull away from the casting. This further aids in removal of the dental cast from the mold. The mold can also be reused.

This invention has been described in its presently preferred best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A dental articulator comprising:
   first and second bodies being attached together by at least first, second and third legs, each of said first, second and third legs having a self-hinge, said first and second bodies and said first, second and third legs being unitarily molded of synthetic polymer composition material;
   first and second attachment members;
   first and second ball and socket attachment means, respectively, between said first and second bodies and said first and second attachment members, said ball and socket attachment means being such that ball and socket attachment means can be selectively locked to lock said attachment members in position with respect to said body;
   first and second tapered spines respectively formed on said first and second attachment members, said spines being configured to be releasably inserted into a corresponding recess in a dental cast so that the spline can be removed from one dental cast and used in another dental cast.

2. The dental articulator of claim 1 wherein said first and second bodies and said hinges comprise a main member, said main member being integrally molded of synthetic polymer composition material.

3. The dental articulator of claim 1 wherein said ball and socket means comprise a ball positioned within a socket.

4. The dental articulator of claim 3 wherein said socket is in said body and said ball is mounted on said attachment member.

5. The dental articular of claim 4 wherein said ball is rough to provide secure locking of said ball within said socket.

6. The dental articulator of claim 4 further including a locking plunger, said locking plunger having at least one sharp member thereon which engages both said ball and said socket to lock said ball in said socket.

7. The dental articulator of claim 3 wherein said first and second sockets are respectively in said first and second bodies and there are first and second socket caps respectively mounted on first and second levers, said first and second levers and said first and second caps being respectively molded with said first and second bodies.

8. The dental articular of claim 7 wherein said first and second levers are finger levers and have finger engagement means thereon to aid in manually closing said ball within said socket.

9. The dental articulator of claim 8 wherein said caps have latches thereon and said finger levers are positioned to disengage said latches to release said caps for repositioning said ball within said socket.

10. The dental articulator of claim 9 further including a locking plunger, said locking plunger having at least one sharp member thereon which engages both said ball and said socket to lock said ball in said socket.

11. A dental articulator comprising:
a main member, first and second bodies on said main member, first and second legs interconnecting said bodies, each of said legs having a self-hinge therein, said main member being unitarily molded of synthetic polymer composition material;
first and second attachment members, each of said first and second attachment members having a tapered spline thereon, said tapered spline being for engaging in a corresponding mold recess in a dental cast for releasable engagement in the dental cast; and
first and second ball and socket means formed on said first and second body and said first and second attachment members for permitting adjustment of said first and second attachment members with respect to said first and second bodies and locking of said first and second attachment members with respect to said first and second bodies, the portion of said ball and socket means on said bodies being molded therewith.

12. The dental articulator of claim 11 further including in combination a dental cast having a recess therein corresponding to said tapered spline so that said dental cast is releasably mounted on said tapered spline for positioning by said articulator.

13. The dental articulator of claim 12 wherein there is a thumb pad on said tapered spline and a corresponding thumb pad recess in said dental cast.

14. The dental articulator of claim 11 wherein said ball and socket means comprises a socket on said body and a ball on said attachment member.

15. The dental articulator of claim 14 further including first and second caps respectively mounted on said first and second bodies for respectively covering said first and second sockets, said caps being integrally molded with said main member.

16. The dental articulator of claim 15 further including a latch on each of said caps so that said caps can be releasably latched over the corresponding socket for retention of a ball in said socket.

17. The dental articulator of claim 15 further including a locking plunger, said locking plunger having a sharp member thereon, said locking plunger engaging both said main member and said ball to lock said ball within its socket.

18. A dental articulator comprising:
first and second attachment members, each of said first and second attachment members having a tapered spline thereon;
a dental cast mold, said dental cast mold having a spear therein configured to produce a spline recess in a dental cast molded therein of such configuration as to releasably retain said spline; and
a main member adjustably attached to both said attachment members so that said attachment members can be adjusted with respect to each other to adjust dental casts with respect to each other.

19. The dental articulator of claim 18 wherein said spline has a thumb pad thereon and said spear has a base thereunder so that a pad recess is molded adjacent said spline recess so that said spline and said thumb pad are releasably inserted into a corresponding recess in the dental cast.

20. The dental articulator of claim 19 wherein said main member comprises first and second bodies and said attachment members are adjusably mounted with respect to said first and second bodies, at least first and second legs between said bodies and a self-hinge in each of said legs to permit said bodies to be positioned with respect to each and to be moved away from each other, said main member being molded of synthetic polymer composition material.

* * * * *